(12) United States Patent
Wojke et al.

(10) Patent No.: US 10,220,133 B2
(45) Date of Patent: Mar. 5, 2019

(54) METHOD OF PURGING GAS BUBBLES IN AN EXTRACORPOREAL BLOOD CIRCUIT

(71) Applicant: FRESENIUS MEDICAL CARE DEUTSCHLAND GMBH, Bad Homburg (DE)

(72) Inventors: Ralf Wojke, Bad Homburg (DE); Paul Wieneke, Muenster (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 14 days.

(21) Appl. No.: 15/501,547

(22) PCT Filed: Aug. 5, 2015

(86) PCT No.: PCT/EP2015/001617
§ 371 (c)(1),
(2) Date: Feb. 3, 2017

(87) PCT Pub. No.: WO2016/020060
PCT Pub. Date: Feb. 11, 2016

(65) Prior Publication Data
US 2017/0232179 A1     Aug. 17, 2017

(30) Foreign Application Priority Data

Aug. 5, 2014    (DE) .................. 10 2014 011 673

(51) Int. Cl.
*A61M 1/36*      (2006.01)
*A61M 39/28*     (2006.01)
*A61M 39/22*     (2006.01)

(52) U.S. Cl.
CPC ........ *A61M 1/3627* (2013.01); *A61M 1/3626* (2013.01); *A61M 1/3643* (2013.01);
(Continued)

(58) Field of Classification Search
None
See application file for complete search history.

(56) References Cited

U.S. PATENT DOCUMENTS 4,486,303 A * 12/1984 Brous ................. A61M 1/16
                                                   210/321.65
5,863,421 A *  1/1999 Peter, Jr. ................ A61L 2/04
                                                        210/108
(Continued)

FOREIGN PATENT DOCUMENTS

| EP | 1837045 | 9/2007 |
|----|---------|--------|
| EP | 2535065 | 12/2012 |
| JP | 2004313522 | 11/2004 |

*Primary Examiner* — Krishnan S Menon
*Assistant Examiner* — Bradley R Spies
(74) *Attorney, Agent, or Firm* — Jacobson Holman, PLLC.

(57) ABSTRACT

The invention relates to a method of purging gas bubbles from a target zone of an extracorporeal blood circuit of a dialysis machine, wherein the target zone is flowed through by flushing liquid which enters into the target zone through an inflow and exits it again through an outflow, wherein the inflow differs from the arterial port and the outflow differs from the venous port of the extracorporeal blood circuit. The invention furthermore relates to a dialysis machine having an extracorporeal blood circuit and a control unit, with the extracorporeal blood circuit having an inflow and an outflow for flushing liquid, with the inflow differing from the arterial port and the outflow differing from the venous port of the extracorporeal blood circuit, and with the control unit being configured to carry out a method in accordance with the invention. The invention furthermore relates to a disposable for the dialysis treatment, wherein the disposable comprises an arterial line, elements of a blood pump, a dialyzer and a venous line, wherein the disposable has an interface for the inflow of flushing liquid in the arterial line and an interface (Continued)

Figure 1:
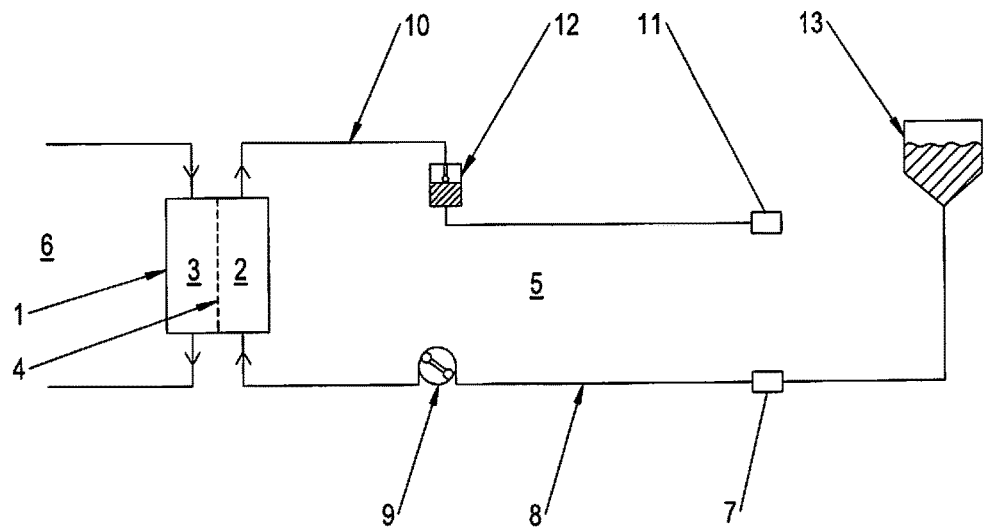

for the outflow of flushing liquid in the venous line, and wherein the interface for the inflow differs from the arterial port and the interface for the outflow differs from the venous port of the hose set.

12 Claims, 2 Drawing Sheets

(52) U.S. Cl.
CPC ........ *A61M 1/3644* (2014.02); *A61M 1/3672* (2013.01); *A61M 39/223* (2013.01); *A61M 39/28* (2013.01); *A61M 2205/3331* (2013.01); *A61M 2205/3334* (2013.01)

(56) References Cited

U.S. PATENT DOCUMENTS

| | | | |
|---|---|---|---|
| 5,951,870 A | 9/1999 | Utterberg | |
| 6,171,484 B1* | 1/2001 | Schnell | A61M 1/3627 138/89 |
| 6,454,736 B1 | 9/2002 | Ludt et al. | |
| 6,610,027 B1* | 8/2003 | El Hatu | A61M 1/16 604/4.01 |
| 2006/0213835 A1* | 9/2006 | Nimura | A61M 1/3643 210/645 |
| 2009/0294359 A1* | 12/2009 | Hopping | A61M 1/28 210/646 |
| 2011/0213289 A1 | 9/2011 | Toyoda et al. | |
| 2014/0110319 A1 | 4/2014 | Coulthard et al. | |

* cited by examiner

METHOD OF PURGING GAS BUBBLES IN AN EXTRACORPOREAL BLOOD CIRCUIT

The invention relates to a method of purging gas bubbles from a target zone of an extracorporeal blood circuit, to an extracorporeal blood treatment unit and to a disposable for the extracorporeal blood treatment.

Microbubbles are gas bubbles having a diameter of a few μm which as a rule are no longer visible due to their small size. They arise at different points and under different conditions in extracorporeal blood circuits, inter alia by the discharge of blood-soluble gases or by air entry at very small leaks in the vacuum region of the extracorporeal circuit, and adhere to the inner surface of the extracorporeal hose system or of the blood treatment unit. Their effects when they are detached and infuse into the human body are greater than previously presumed. For example, microbubbles were found in vital organs such as the lung, heart and brain of dialysis patients.

Observations at dialyzers with the aid of a microbubble detector allow a number of possible sources for microbubbles to be recognized. It was inter alia observed that an increased entry of microbubbles into the patient takes place in the first minutes of the treatment. At the start, the mean microbubble flow can be an order of magnitude higher than during the remaining treatment. In addition, there are potentially air collections in the extracorporeal circuit which can serve as sources and reservoirs for later microbubble formation. Air collections can, for example, be present in the dialyzer, in the hose segment of the blood pump, in the venous drip chamber, in heparin syringes and in other injection syringes, in supplying lines (e.g. in a heparin hose) and in further interfaces (e.g. Luer connections). The vacuum in the intake region of the pump generally promotes air inputs. Furthermore, an increased number of microbubbles was observed during a pressure holding test in which the dialysis fluid is temporarily no longer refreshed and the blood in the dialyzer capillaries is no longer washed around with fresh, degased dialysis fluid.

Microbubbles can only be separated with limitations in the venous chamber due to their small size and their small buoyancy and can only be conditionally recognized by the prescribed protection system for avoiding air infusion.

It is the underlying object of the invention to reduce the number of microbubbles in extracorporeal blood circuits or to reduce the infusion of microbubbles into the patient's body.

Against this background, the invention proposes a method of purging gas bubbles from a target zone of an extracorporeal blood circuit, wherein the target zone is flowed through by a flushing liquid which enters into the target zone through an inflow and exits again through an outflow. Provision is made in accordance with the invention that the inflow differs from the arterial port and the outflow differs from the venous port of the extracorporeal blood circuit.

In an embodiment, the extracorporeal blood circuit is that of a dialysis machine. The extracorporeal blood circuit of a dialysis machine comprises an arterial line, a blood pump, a dialyzer and a venous line. An arterial port for connection to a patient is arranged in the arterial line. A venous port for connection to the patient is arranged in the venous line. In accordance with the invention, the flushing liquid does not leave the target zone via the venous port, but rather via a separate outflow. A higher flexibility with respect to the onset time of the method of purging gas bubbles can thereby be achieved. Since known processes from the prior art used the venous port as the outflow or required a short-circuit of the venous port, a purging of gas bubbles could not take place while a patient was connected to the circuit. For example, a purging of gas bubbles was not possible during a treatment break, for example during a pressure holding test.

Furthermore, a use of the method is also conceivable in other extracorporeal treatment systems, for example in ultrafiltration devices and heart-lung machines.

The target zone represents a portion of the extracorporeal blood circuit which lies between the inflow and the outflow. Since the inflow differs from the arterial port and the outflow differs from the venous port, the target zone only comprises a part section of the extracorporeal blood circuit. Different portions or functional groups of the extracorporeal blood circuit can lie outside the target zone in different embodiments. For example, a blood pump preferably arranged in the venous line can lie outside the target zone.

The target zone is preferably flowed through in the forward direction. The forward direction is defined so that the flushing liquid flows in the direction of the venous port. The terms "upstream" and "downstream" relate within the framework of the present invention to the provided flow direction in the extracorporeal blood circuit. The flushing liquid preferably always runs through the target zone in the same direction during the total process. The flushing liquid is preferably not circulated during the process. Provision can, however, be made from case to case that a circulation takes place at least at times to the effect that consumed flushing liquid is optionally reused after a processing.

In an embodiment, the outflow is arranged in the venous line. In an embodiment, the outflow is arranged downstream of all existing interfaces of the extracorporeal blood circuit. Examples of existing interfaces comprise a predilution port, a postdilution port, a port for administering anticoagulants (e.g. heparin or citrate), a port for blood taking, a port for arterial or venous medication administration or the like. The arterial and venous ports are not understood as interfaces in the sense of this embodiment. Provided that the outflow is arranged downstream of all existing interfaces of the extracorporeal blood circuit, a portion of the extracorporeal blood circuit which is as large as possible can be freed of microbubbles and can be wetted in the case of a simultaneously administered anticoagulant. The outflow is preferably close to the venous port. It is, however, advantageous to arrange the outflow upstream of any protective systems against air injection such as an air bubble detector.

In an embodiment, the inflow is arranged in the arterial line. In an embodiment, the inflow is arranged upstream of the blood pump. The inflow can alternatively be arranged downstream of the blood pump. The access of the substitute flow can generally lie close to the arterial port to be able to free a portion of the hose system which is as large as possible from microbubbles. In the case of a desired intermittent flushing with an anticoagulant, the access of the substitute flow should preferably lie upstream of the hose for administering the anticoagulant to take along the simultaneously administered anticoagulant and to wet a portion of the hose system which is as large as possible. The access is therefore disposed in an embodiment upstream of the blood pump. Alternatively, an arrangement of the inflow downstream of the blood pump is also conceivable, and optionally upstream of an interface for the anticoagulant administration (e.g. heparin).

In an embodiment, existing interfaces are used as the inflow. Examples of existing interfaces which can be used as the inflow comprise a predilution port or a port for the administration of anticoagulants. In an embodiment, the extracorporeal blood circuit has an inflow configured as a separate interface. Provision can be made in a conceivable embodiment, for example, that an additional inflow is arranged upstream of the blood pump so that the region around the blood pump can also be flushed or freed of microbubbles.

The target zone preferably comprises such sections of the extracorporeal blood circuit in which a gas bubble formation or gas bubble deposition frequently occurs. Provided that the inflow is arranged in the arterial line and the outflow is arranged in the venous line, the target zone at least comprises the dialyzer in the case of a dialysis machine. If the inflow is arranged upstream of the blood pump, the target zone furthermore comprises the blood pump. Further portions which can be covered by the target zone comprise the venous drip chamber, heparin injection syringes and other injection syringes or supply lines generally (e.g. connected via a Luer connection) such as a heparin hose.

In an embodiment, the extracorporeal blood circuit comprises an arterial and/or a venous clamp. The arterial clamp is preferably arranged between the arterial port and the inflow. The venous clamp is preferably arranged between the outflow and the venous port. An arterial clamp can then be dispensed with, for example, provided that the inflow is arranged downstream of the blood pump. For a stationary blood pump can also develop a corresponding blocking effect. The term of a clamp in the present case also comprises a blocking valve.

In an embodiment, the inflow and/or the outflow can be closed using a clamp. In an embodiment, the inflow and/or the outflow is/are connected to the extracorporeal blood circuit using a three-way valve. A clamp is to be understood as a means which is suitable to block the arterial line or the venous line respectively. Using a three-way valve, the arterial port or the inflow can alternatively be decoupled from the target zone at the upstream end of the target zone and the venous port or the outflow can be decoupled from the target zone at the downstream end of the target zone.

In an embodiment, the flow rate and/or the pressure of the flushing liquid in the extracorporeal blood circuit is inconstant at least at times during the flushing process. A more efficient detachment of microbubbles from the walls of the extracorporeal blood circuit can thus be achieved. The variation of the flow rate and/or of the pressure can take place by a change of the conveying rate of a pump or by a control of a clamp or of a valve. In an embodiment, the flow rate and/or the pressure of the flushing liquid is increased and reduced in bursts. The bursts can show a continuous or abrupt build-up and a continuous or abrupt drop in the flow rate and/or in the pressure of the flushing liquid. The amplitude of the bursts can be selected such that the flow rate and/or the pressure of the flushing liquid varies between valleys and peaks by at least a factor of 1.3, a factor of 1.5 or a factor of 2.

In an embodiment, the flow rate of the flushing liquid in the extracorporeal blood circuit lies outside a range of possible flow rates at least at times during the flushing process. The latter feature can mean that the flow rate of the flushing liquid in the extracorporeal blood circuit lies above a range of possible flow rates at least at times during the flushing process, which range is used during the treatment for the blood. There is further the possibility of flow reversal, for example. In an embodiment, the flow rate of the flushing liquid in the extracorporeal blood circuit during the flushing process is larger than 550 ml/min or larger than 700 ml/min at least at times. In many cases, a flow of between 200 ml/min and 550 ml/min is selected during an extracorporeal blood treatment, in particular when hose systems having an internal diameter of between 3 and 5 mm are used. A higher flow rate during the flushing process can result in a better detachment of gas bubbles.

In an embodiment, the method can be carried out within the framework of the priming of the extracorporeal blood circuit and can, for example, represent the final step of the priming procedure.

In an embodiment, the method is carried out during a treatment interruption, in particular during a pressure holding test. The method can be triggered manually or automatically. Examples for trigger conditions comprise a periodic triggering (e.g. with interval magnitudes of 30 minutes to 2 hours) or a triggering in response to specific sensor reports (e.g. measured value of the bubble detector exceeds a limit value) or events (e.g. start of a pressure holding test). The flushing can take place over a predefined time period (e.g. with a duration of between 1 and 5 minutes) or can be determined manually or automatically on the basis of different parameters. The coupling to a duration of another process such as a pressure holding test is also conceivable.

In an embodiment, the process comprises the following steps: (a) Closing an arterial clamp and opening the inflow; (b) Conveying a first volume of flushing liquid into the target zone, with the first volume substantially corresponding to the volume of the target zone; (c) Closing a venous clamp and opening the outflow; (d) Flushing through of the target zone with the flushing liquid; (e) Opening the arterial clamp and closing the inflow; (f) Draining of a second volume of flushing liquid from the target zone, with the second volume substantially corresponding to the volume of the target zone; and (g) Closing the outflow and opening the venous clamp. In this embodiment, the inflow is preferably arranged upstream of the blood pump.

The conveying of the flushing liquid in steps (b), (d) and (f) preferably takes place using the blood pump.

In an embodiment, the process comprises the following steps: (a') Stopping the blood pump and opening the inflow; (b') Conveying a first volume of flushing liquid into the target zone, with the first volume substantially corresponding to the volume of the target zone; (c') Closing a venous clamp and opening the outflow; (d') Flushing through of the target zone with the flushing liquid; (e') Closing the inflow and starting the blood pump; (f') Draining of a second volume of flushing liquid from the target zone, with the second volume substantially corresponding to the volume of the target zone; and (g') Closing the outflow and opening the venous clamp. In this embodiment, the inflow is preferably arranged downstream of the blood pump. The conveying of the flushing liquid in steps (b') and (d') preferably takes place using a separate flushing pump. The conveying of the flushing liquid in step (f') preferably takes place using the blood pump.

The method steps preferably take place in the named order (a) to (g) or (a') to (g') respectively. In an embodiment, the feature that the first or second volume 'substantially' corresponds to the volume of the target zone can designate a maximum difference of ±20% or ±10%. This reflects the fact that frequently no exact corresponding is necessary, but an approximate correspondence is advantageous. If a difference occurs, the quantity of the supplied flushing liquid or of the drained blood can be detected and processed on the determination by a control unit. As a further consequence, this can result, for example, in a taking into account on the determination of treatment-specific parameters, in particular in the determination of the ultrafiltration volume. The closing and opening in steps (a) and (e) or (a') and (e') respectively and in steps (c) and (g) or (c') and (g') respectively can take place by a switchover of a three-way valve.

Against the initially described background, the invention furthermore relates to an extracorporeal blood treatment unit having an extracorporeal blood circuit and a control unit, with provision being made in accordance with the invention that the extracorporeal blood circuit has an inflow and an outflow for flushing liquid, with the inflow differing from the arterial port and the outflow differing from the venous port of the extracorporeal blood circuit, and with the control unit being configured to carry out a method in accordance with the invention.

The feature that the control unit is configured to carry out a method in accordance with one of the preceding claims means that a corresponding routine is stored in the control unit and that the control unit is connected to the necessary actuators (e.g. pumps and valves) which are required for carrying out the method. The extracorporeal blood treatment unit can comprise constructional features which were described in connection with the method in accordance with the invention.

In an embodiment, the extracorporeal blood treatment unit is a dialysis machine. The dialysis machine can be suitable and intended for carrying out a hemodialysis, a hemodiafiltration, a hemofiltration and/or an ultrafiltration (only liquid removal). Furthermore, the extracorporeal blood treatment unit in accordance with the invention can be another treatment system, for example an ultrafiltration device or a heart-lung machine.

In an embodiment, the blood treatment unit comprises a line system for flushing liquid which is connected to the extracorporeal blood circuit so that flushing liquid can enter into the target zone through an inflow and can leave it again through an outflow, with the line system preferably comprising a flushing pump which is arranged upstream of the inflow in the line system.

In an embodiment, the line system comprises a reservoir for flushing liquid or a preparation unit for flushing liquid, each arranged upstream of the inflow in the line system. The control unit can be connected to the flushing pump and can be configured such that it controls the flushing pump within the framework of the method in accordance with the invention to effect a flushing of the target zone.

In an embodiment, the control unit is configured so that it automatically triggers the process within the framework of the priming of the extracorporeal blood circuit. The process can, for example, represent the final priming step.

In an embodiment, the control unit is configured so that it interrupts the treatment before the carrying out of the process and/or so that it triggers the process during an interruption of the treatment and/or so that it automatically continues the treatment after the carrying out of the process. The control unit can, for example, be configured to interrupt the treatment just to carry out the process. The interruption takes place periodically, for example (e.g. with interval values from 30 minutes to 2 hours) or in response to specific sensor reports, for example reports of a gas bubble sensor arranged in the venous line. The control unit can furthermore be configured so that the process is triggered when the treatment is anyway interrupted. The process can be triggered, for example, during a pressure holding test. The duration of the process can, for example, correspond to the duration of a simultaneously carried out pressure holding test (e.g. between 1 and 5 minutes).

In an embodiment, the control unit is configured so that it takes account of the quantity of flushing liquid supplied by the process and/or of blood led off by the process in the determination of treatment-specific parameters, in particular in the determination of the ultrafiltration volume.

In an embodiment, the control unit is configured so that the conveying speed for blood is slowly increased at the end of the process. It can thus be achieved that fewer microbubbles are detached into the blood at the start of the blood treatment. For example, the conveying speed is increased on an optionally linear ramp with an increase of no more than 300 ml/min$^2$ or 200 ml/min$^2$ or 150 ml/min$^2$.

The blood pump and/or the flushing pump can be a peristaltic pump. The flushing liquid can, for example, be a substitution solution or a priming solution. Examples comprise physiological saline and Ringer's solution. The solution can furthermore optionally contain anticoagulants such as heparin.

Against the initially described background, the invention furthermore relates to a disposable for the extracorporeal blood treatment, with the disposable comprising an arterial line, elements of a blood pump, a blood treatment unit and a venous line.

Provision is made in accordance with the invention that the disposable in the arterial line has an interface for the inflow of flushing liquid and in the venous line has an interface for the outflow of flushing liquid, with the interface for the inflow differing from the arterial port and the interface for the outflow differing from the venous port of the hose set.

In an embodiment, the disposable is a disposable for the dialysis treatment and the blood treatment unit is a dialyzer. Furthermore, the disposable in accordance with the invention can be a fluid system of an ultrafiltration unit or of a heart-lung machine.

The blood pump can be completely integrated in the disposable; however, for cost reasons it appears expedient to arrange the pump at the machine side and only to arrange certain elements of the pump at the disposable which interact with further elements of the pump arranged at the machine side and form a pump together. An example is a peristaltic pump, with an elastically deformable hose segment being able to be arranged at the disposable and with actuators of a pump which are arranged at the machine side engaging into said hose segment.

The disposable preferably comprises a blood hose set, with the arterial line and the venous line being configured at least sectionally as a blood hose. The inner diameter of the blood hoses amounts to between 3 and 5 mm, for example. The disposable can be produced from plastic at least in part. The blood treatment unit is preferably a hollow fiber dialyzer.

In an embodiment, the interface for the inflow and/or the interface for the outflow of flushing liquid has/have elements of a mechanical connection system. These connection elements preferably comprise a female cone of a Luer Lock or of a Luer slip. The disposable can thereby be used in a variety of manners since a male Luer cone can be found at a number of connections of existing units at the machine side.

The disposable can be used in a method in accordance with the invention and in a blood treatment unit in accordance with the invention.

In an embodiment, the interface for the outflow of flushing liquid is arranged downstream of all other interfaces of the disposable. Examples of existing interfaces comprise an interface for a predilution, an interface for a postdilution, an interface for the administration of anticoagulants, an interface for blood taking and interfaces for the arterial or venous medication administration or the like. The arterial and venous ports are not understood as interfaces in the sense of this embodiment.

In an embodiment, the interface for the inflow of flushing liquid is arranged upstream of the pump segment. Provision can alternatively be made that the interface for the inflow of flushing liquid is arranged downstream of the pump segment. In an embodiment, existing interfaces are used as an interface for the inflow of flushing liquid. Examples comprise an interface for the predilution or an interface for the administration of anticoagulants. In another embodiment, the disposable has a separate interface for the inflow of flushing liquid.

In an embodiment, the extracorporeal blood circuit comprises an arterial clamp and/or a venous clamp, with the elements of the arterial clamp preferably being arranged between the arterial port and the interface for the inflow of flushing liquid and with the venous clamp preferably being arranged between the interface for the outflow of flushing liquid and the venous port.

In an embodiment, the interface for the inflow and/or outflow of flushing liquid can be closed using a clamp or can be connected to the arterial line or to the venous line using a three-way valve. The clamp can be completely integrated in the disposable. An example comprises a blocking valve. Generally, only certain elements of the clamp can also be arranged at the disposable, the elements interacting with further elements of the clamp arranged at the machine side and together forming a clamp. An example is an elastically deformable (hose) segment at the disposable in interaction with an actuator arranged at the machine side.

Figure 2:
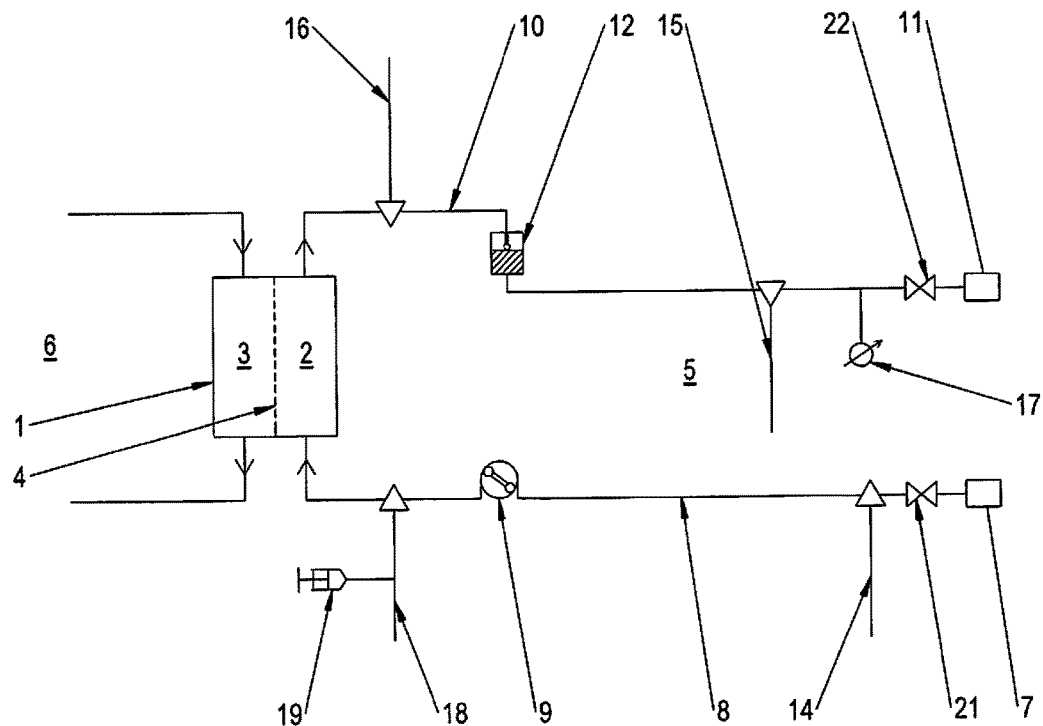
Figure 3:
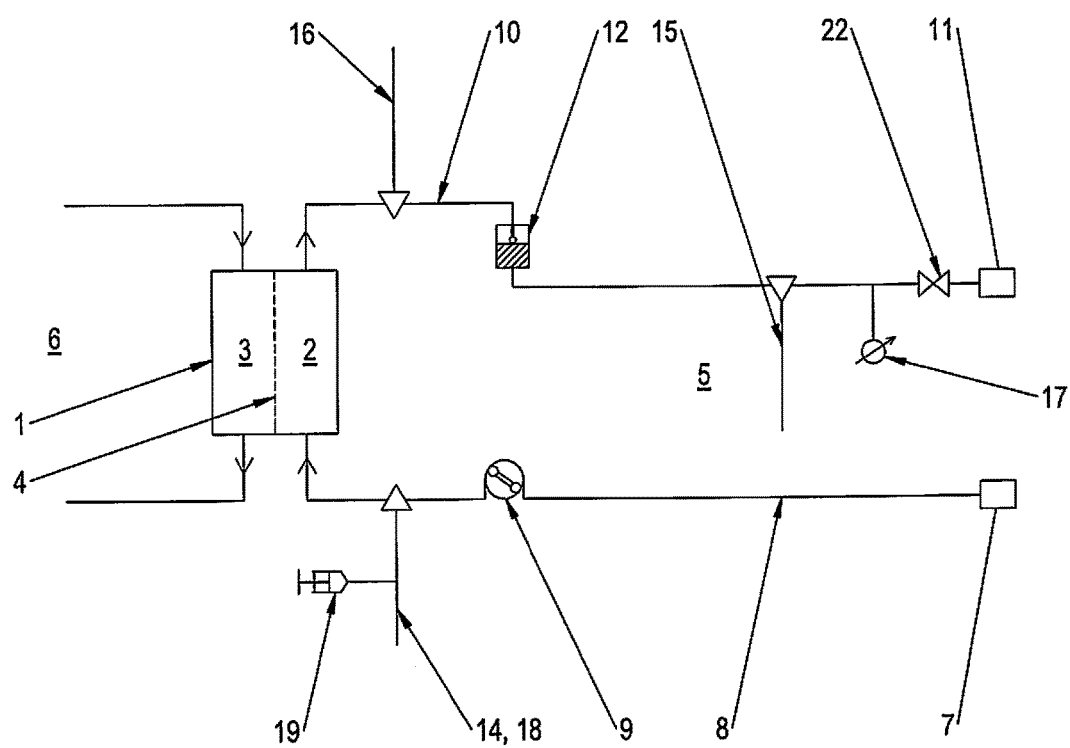

Further details and advantages result from the Figures and embodiments described in the following. There are shown in the Figures:

FIG. 1: a schematic representation of fluid circuits of a dialysis machine from the prior art;

FIG. 2: a schematic representation of fluid circuits in accordance with a dialysis machine in accordance with a first embodiment of the invention; and FIG. 3: a schematic representation of fluid circuits in accordance with a dialysis machine in accordance with a second embodiment of the invention.

FIG. 1 shows fluid circuits of a dialysis machine from the prior art. The dialysis machine has a dialyzer 1 which has a blood chamber 2 and a dialysis liquid chamber 3 which are separated from one another by a membrane 4. The blood chamber 2 is a component of an extracorporeal blood circuit 5. The dialysis liquid chamber 3 is a component of a dialysis liquid circuit 6.

The blood circuit 5 has an arterial port 7 which is connected to the blood chamber 2 via an arterial line 8. A blood pump 9 is seated in the arterial line 8. The venous end of the blood chamber 2 is connected to the venous port 11 by means of the venous line 10. A drip chamber 12 is located in the venous line.

The arterial and venous ports are not connected to the patient during the filling and flushing (priming) of the blood circuit. The arterial port is connected to a flushing liquid reservoir 13 and the venous port represents an outflow for flushing liquid. After the filling of the blood circuit with flushing liquid, a flushing phase takes place, with flushing liquid exiting the venous port.

A flushing of the blood circuit can thus not take place while a patient is connected to the circuit since the arterial port and the venous port are not available for the flushing.

FIG. 2 shows fluid circuits of a dialysis machine in accordance with a first embodiment of the invention. Components already known from FIG. 1 are provided with corresponding reference numerals.

Unlike the prior art, the extracorporeal blood circuit 5 furthermore here has a separate inflow 14 and a separate outflow 15 for flushing liquid. It is thus made possible that the flushing liquid cannot leave a target zone for a flushing disposed between the inflow and the outflow via the venous port 11, but rather via the separate outflow 15. Flushing liquid can furthermore enter into the circuit via a separate inflow.

The outflow 15 is arranged in the venous line 10 downstream of all existing interfaces of the extracorporeal blood circuit. A postdilution port 16 is shown as an interface by way of example in the Figure. An air bubble detector 17 is located between the outflow and the venous port. The inflow is arranged upstream of the blood pump in the arterial line and represents a separate access. As a further interface, the blood circuit comprises a predilution port 18 with an integrated heparin feed line 19. The extracorporeal blood circuit furthermore comprises an arterial clamp 20 and a venous clamp 21. The arterial clamp is arranged between the arterial port 7 and the inflow 14. The venous clamp is arranged between the outflow 15 and the venous port 11. Both the inflow 14 and the outflow 15 are connected to the extracorporeal blood circuit 15 by means of a three-way valve.

A higher flexibility with respect to the onset time of the method for purging gas bubbles can be achieved by the arrangement of the additional outflow and inflow as well as by the further components of the dialyzer in accordance with the invention. For example, a purging of gas bubbles is possible during a treatment break, for example during a pressure holding test. A flushing can, for example, have the following steps before or during the treatment:

(a) Closing the arterial clamp and opening the inflow;
(b) Conveying a first volume of flushing liquid into the target zone disposed between the inflow and outflow, with the first volume substantially corresponding to the volume of the target zone;
(c) Closing the venous clamp and opening the outflow;
(d) Flushing through of the target zone with the flushing liquid;
(e) Opening the arterial clamp and closing the inflow;
(f) Draining of a second volume of flushing liquid from the target zone, with the second volume substantially corresponding to the volume of the target zone; and
(g) Closing the outflow and opening the venous clamp.

The conveying of the flushing liquid in steps (b), (d) and (f) takes place using the blood pump. The conveying of the flushing liquid into the system takes place using a separate flushing pump which is not shown in the Figures and which is arranged in the supply system for the flushing liquid at the machine side.

Provided that, as in the shown embodiment, the access of the substitute flow is disposed before the blood pump, the flushing out of the microbubbles can be carried out in that the substitute pump and the blood pump run at the same conveying rate. Since the substitute is then completely conveyed on at the same conveying rate by the blood pump, blood can no longer be drawn into the hose system so that an arterial clamp can also be dispensed with. Alternatively, an arterial clamp allows the temporary clamping closed of the blood stream and allows large freedom with respect to a variation of the conveying rates of the blood pump and the substituate pump for generating pressure pulses and volume flow pulses which can be suitable to detach and take along bubbles and microbubbles.

FIG. 3 shows fluid circuits of a dialysis machine in accordance with a further embodiment of the invention. Components already known from FIGS. 1 and 2 are provided with corresponding reference numerals.

This embodiment differs from the embodiment shown in FIG. 1 in that the inflow 14 is arranged downstream of the blood pump in the arterial line and corresponds to the predilution port 18 with an integrated heparin feed line 19. An arterial clamp has been dispensed with. For example, a flushing can have the following steps before or during the treatment using this embodiment of the invention:

(a') Stopping the blood pump and opening the inflow;
(b') Conveying a first volume of flushing liquid into the target zone disposed between the inflow and outflow, with the first volume substantially corresponding to the volume of the target zone;
(c') Closing the venous clamp and opening the outflow;
(d') Flushing through of the target zone with the flushing liquid;
(e') Closing the inflow and starting the blood pump;
(f') Draining of a second volume of flushing liquid from the target zone, with the second volume substantially corresponding to the volume of the target zone; and
(g') Closing the outflow and opening the venous clamp.

The conveying of the flushing liquid in steps (b') and (d') takes place using a separate flushing pump which is not shown in the Figures and which is arranged in the supply system for the flushing liquid at the machine side. The conveying of the flushing liquid in step (f') preferably takes place using the blood pump 9.

Provided that a purging of the target zone takes place using a dialysis machine in accordance with the invention during the carrying out of a pressure holding test in the dialysis liquid circuit, there are two possibilities of process management in both embodiments shown, namely a temporal decoupling and a spatial decoupling.

Temporal decoupling means that the flushing is already initiated before the direct start of the pressure holding test and substitution liquid is flushed into the target zone as the flushing liquid. Spatial decoupling means that a further vessel is used, for example a bag for the buffering of substituate.

During the temporal decoupling, the blood flow in the extracorporeal blood circuit is stopped and is replaced with an addition of the flushing solution into the arterial line. The flushing solution is filled in with a still running blood pump for so long until the boundary layer of substituate/blood close to the body can be detected approximately at the level of the venous chamber, for example by an optical detector or color sensor. The dialysis liquid circuit is then stopped for the pressure holding test. The venous clamp is then closed and the outflow opened. The target zone is flushed using a method in accordance with the invention during the pressure holding test. After the pressure holding test, the extracorporeal circuit is coupled again; an outlet valve close to a vein is opened until the boundary layer blood/substituate now provided with the opposite sign is detected. The outflowing substituate charged with microbubbles is discarded. The outlet valve is now closed and the blood purification is continued. In the spatial decoupling, a further vessel is used for buffering substituate solution and the blood-side system is then fed from this during the pressure holding test. The process management otherwise takes place as with the temporal decoupling.

In both of the embodiments shown, an adaptation of the pump rate to an ideal speed can take place during the flushing using a dialysis machine in accordance with the invention.

Such an adaptation can take place against the background that it has been observed that a high entry of microbubbles into the patient in particular takes place in the first minutes of the treatment. At the start, the mean microbubble flow can be an order of magnitude higher than during the remaining treatment. In addition, there is a number of air collections in the extracorporeal circuit which can serve as a source and reservoir for later microbubble injections (blood pump hose, heparin injection syringes and other injection syringes, supply lines (e.g. heparin hose and other drain lines)). The blood pump rate or flushing pump rate can thus, for example, be operated during the flushing such that the microbubbles can be removed more easily. The partly stationary microbubbles should e.g. be detached by means of a repeated stop and go of the pump and a high pump speed. Flow bursts and pressure bursts attack air collections and microbubble reservoirs and reduce them. These bursts can be achieved e.g. by brief maximum pump rates, blocking and releasing a venous clamp and the like. The detached microbubbles are removed from the extracorporeal circuit by means of the outflow in the venous line.

Furthermore, such an adaptation can take place against the background that it has been observed that the fast start-up of the blood pump can have the consequence of an intense increase of the number of microbubbles and that in particular a pressure holding test, in which the dialysis liquid is no longer refreshed and the blood in the dialyzer capillaries is no longer rinsed around with fresh, degased dialysis liquid, can have the consequence of an intense increase of the number of microbubbles. The blood pump can therefore optionally ramp up slowly after the flushing, e.g. in a ramp at no more than 200 ml/min$^2$, which means that a desired rate of, for example, 400 ml/min is only reached after 2 minutes after a blood pump stop. In the case of a pressure holding test, the blood pump rate can be lowered in good time before the test, the conveying rate of the blood pump and substitution pump can remain at a minimum during the flushing and the pressure holding test and both rates can subsequently ramp up again slowly to their desired value.

It can be stated in summary that the invention makes it possible to flush a target zone of the extracorporeal blood circuit at any desired time, for example during a pressure holding test, and thus to avoid the formation of microbubbles. The flushing liquid can be discarded via the separate outflow.

The invention claimed is:

1. A method of purging gas bubbles from a target zone of an extracorporeal blood circuit useful in a dialysis machine, wherein the target zone is flowed through by a flushing liquid which enters into the target zone through an inflow and exits it again through an outflow, comprising the sequential steps of closing an arterial clamp arranged between the inflow and an arterial port connected to a patient,
opening the inflow,
conveying a first volume flushing liquid into the target zone with the first volume substantially corresponding to the volume of the target zone,
closing a venous clamp arranged between the outflow and a patient,
opening the outflow,
flushing the flushing liquid through the target zone,
opening the arterial clamp, closing the inflow, draining a second volume of flushing liquid from the target zone, with the second volume substantially corresponding to the volume of the target zone, closing the outflow, and opening the venous clamp.

2. A method in accordance with claim 1, characterized in that the outflow is arranged in the venous line; and/or in that the outflow is arranged downstream of all existing interfaces of the extracorporeal blood circuit.

3. A method in accordance with claim 1, characterized in that the inflow is arranged upstream of a blood pump in the arterial line.

4. A method in accordance with claim 1, characterized in that the the inflow is arranged downstream of a blood pump in the arterial time.

5. A method in accordance with claim 1, characterized in that the inflow and the outflow are independently closed using a clamp or connected to the extracorporeal blood circuit using a three-way valve.

6. A method in accordance with claim 1, characterized in that the flow rate and/or the pressure of the flushing liquid in the extracorporeal blood circuit is/are inconstant at least at times during the flushing process; and/or in that the flow rate of the flushing liquid in the extracorporeal blood circuit lies outside a range of possible flow rates at least at times during the flushing process, which range is used during the treatment for the blood.

7. A method in accordance with claim 1, characterized in that the method is carried out during a treatment interruption for a pressure holding test.

8. An extracorporeal blood treatment unit useful as a dialysis machine comprising (a) an extracorporeal blood circuit having an arterial port and a venous port and (b) a control unit, characterized in that the extracorporeal blood circuit has an inflow and an outflow for flushing liquid, with the inflow located downstream from the arterial port and the outflow located upstream from the venous port, and the control unit is configured to carry out the method in accordance with claim 1.

9. An extracorporeal blood treatment unit in accordance with claim 8, characterized in that the extracorporeal blood treatment unit comprises a line system for flushing liquid which is connected to the extracorporeal blood circuit so that flushing liquid can enter into the target zone through an inflow and can leave it again through an outflow, with the line system preferably comprising a flushing pump which is arranged upstream of the inflow in the line system.

10. An extracorporeal blood treatment unit in accordance with claim 8, characterized in that the control unit is configured so that it interrupts the treatment before the carrying out of the process and/or so that it triggers the process during an interruption of the treatment and/or so that it automatically continues the treatment after the carrying out of the process.

11. An extracorporeal blood treatment unit in accordance with claim 8, characterized in that the control unit is configured so that it takes account of the quantity of flushing liquid supplied by the process and/or of the blood drained off by the process in the determination of treatment-specific parameters, in particular in the determination of the ultrafiltration volume.

12. An extracorporeal blood treatment unit in accordance with claim 8, characterized in that the control unit is configured so that the conveying speed for blood is increased stepwise after the end of the process.

* * * * *